(12) United States Patent
Gutzeit

(10) Patent No.: US 11,717,247 B2
(45) Date of Patent: Aug. 8, 2023

(54) BLOOD FLOW CONTROL SYSTEM AND METHODS FOR IN-VIVO IMAGING AND OTHER APPLICATIONS

(71) Applicant: Andreas Gutzeit, Zürich (CH)

(72) Inventor: Andreas Gutzeit, Zürich (CH)

(*) Notice: Subject to any disclaimer, the term of this patent is extended or adjusted under 35 U.S.C. 154(b) by 1707 days.

(21) Appl. No.: 14/910,288

(22) PCT Filed: Oct. 14, 2014

(86) PCT No.: PCT/CH2014/000151
§ 371 (c)(1),
(2) Date: Feb. 5, 2016

(87) PCT Pub. No.: WO2015/054800
PCT Pub. Date: Apr. 23, 2015

(65) Prior Publication Data
US 2016/0192893 A1   Jul. 7, 2016

(30) Foreign Application Priority Data

Oct. 18, 2013 (CH) ..................... 1787/13

(51) Int. Cl.
*A61B 6/00* (2006.01)
*A61B 8/06* (2006.01)
(Continued)

(52) U.S. Cl.
CPC .............. *A61B 6/507* (2013.01); *A61B 5/055* (2013.01); *A61B 5/08* (2013.01); *A61B 6/032* (2013.01);
(Continued)

(58) Field of Classification Search
None
See application file for complete search history.

(56) References Cited

U.S. PATENT DOCUMENTS 1,729,294 A * 9/1929 Newell ................. A61B 5/091
600/540
4,403,616 A 9/1983 King
(Continued)

FOREIGN PATENT DOCUMENTS

BR      0212874 A2    6/2011
CA      2460201 A1    4/2003
(Continued)

OTHER PUBLICATIONS

Respiratory rate, by Wikipedia; pub. online on Dec. 1, 2019, accessed Mar. 30, 2020; url = <https://en.wikipedia.org/w/index.php?title= Respiratory_rate&oldid=928745768> (Year: 2019).*
(Continued)

*Primary Examiner* — Christopher Koharski
*Assistant Examiner* — Michael S Kellogg
(74) *Attorney, Agent, or Firm* — Paul D. Bianco; Stephen Bongini; Fleit Intellectual Property Law

(57) ABSTRACT

A method of and device for acquiring in-vivo images or quantitative/qualitative data (perfusion, blood flow, vascularization, contrast enhancement, selective blood supply management) of interior parts of the human body (20) is described, using an imaging system (21) and including the steps of positioning the body (20) relatively to the imaging system (21), applying a respiratory resistance device (10) to the respiratory system of the body (20), and performing an image acquisition step during or concomitantly an inhalation/inspiration/suction or exhalation/Valsalva/expiration phase, during which the body provides suction or exhalation against a resistance as provided by the respiratory resistance device (10).

17 Claims, 4 Drawing Sheets

(51) Int. Cl.
    A61B 5/055      (2006.01)
    A61B 5/08       (2006.01)
    G01R 33/563     (2006.01)
    A61B 8/08       (2006.01)
    G01R 33/565     (2006.01)
    A61B 6/03       (2006.01)
    G01R 33/56      (2006.01)
    A63B 23/18      (2006.01)
    A63B 21/008     (2006.01)

(52) U.S. Cl.
    CPC .............. *A61B 6/481* (2013.01); *A61B 6/504* (2013.01); *A61B 8/06* (2013.01); *A61B 8/481* (2013.01); *G01R 33/56509* (2013.01); *A63B 21/0088* (2013.01); *A63B 23/18* (2013.01); *G01R 33/5601* (2013.01); *G01R 33/563* (2013.01)

(56) References Cited

U.S. PATENT DOCUMENTS

| | | | |
|---|---|---|---|
| 4,640,293 A * | 2/1987 | Garbe | A61B 5/097 128/205.24 |
| 6,567,686 B2 | 5/2003 | Sexton et al. | |
| 6,575,918 B2 | 6/2003 | Kline | |
| 6,631,716 B1 | 10/2003 | Robinson et al. | |
| 6,881,193 B2 | 4/2005 | Kline | |
| 7,019,474 B2 | 3/2006 | Rice et al. | |
| 7,066,892 B2 | 6/2006 | Kline | |
| 7,083,574 B2 | 8/2006 | Kline | |
| 7,104,964 B2 | 9/2006 | Kline | |
| 7,344,497 B2 | 3/2008 | Kline | |
| 7,445,601 B2 | 11/2008 | Kline | |
| 7,447,536 B2 | 11/2008 | Hill | |
| 7,998,084 B2 | 8/2011 | Kline | |
| 2001/0035183 A1* | 11/2001 | Sexton | A61B 5/0813 128/200.24 |
| 2003/0060725 A1 | 3/2003 | Kline | |
| 2003/0062041 A1 | 4/2003 | Keith | |
| 2004/0189265 A1 | 9/2004 | Rice et al. | |
| 2004/0210154 A1 | 10/2004 | Kline | |
| 2005/0245833 A1 | 11/2005 | Kline | |
| 2007/0078357 A1 | 4/2007 | Kline | |
| 2009/0175416 A1* | 7/2009 | Yamanaka | A61B 5/0876 378/95 |

FOREIGN PATENT DOCUMENTS

| | | |
|---|---|---|
| CN | 1511498 A | 7/2004 |
| CO | 5580732 A2 | 11/2005 |
| DE | 10353729 A1 | 5/2005 |
| EP | 1463442 A2 | 10/2004 |
| EP | 1938751 A1 | 7/2008 |
| IL | 161075 A | 12/2010 |
| JP | 2000262513 A | 9/2000 |
| JP | 2005287522 A | 10/2005 |
| JP | 2005529627 A | 10/2005 |
| JP | 437871 B2 | 12/2009 |
| JP | 2012-228387 | 11/2012 |
| JP | 2012-228387 A | 11/2012 |
| MX | 04002038 A | 6/2004 |
| NL | 1024724 A1 | 5/2004 |
| RU | 2009118031 | 11/2010 |
| RU | 2009118031 A | 11/2010 |
| WO | 0174247 A2 | 10/2001 |
| WO | 03026501 A2 | 4/2003 |
| WO | 2013110929 A1 | 8/2012 |

OTHER PUBLICATIONS

MRI contrast agent by Wikipedia, pub. online on Oct. 9, 2013 at <https://en.wikipedia.org/w/index.php?title=MRI_contrast_agent &oldid=576405399> (Year: 2013).*

Intravenous therapy by Wikipedia, pub. online on Sep. 26, 2013 at <https://en.wikipedia.org/w/index.php?title= Intravenous_therapy &oldid=574552385> (Year: 2013).*

Measurement of Caval Blood Flow with MRI During Respiratory Maneuvers: Implications for Vascular Contrast Opacification on Pulmonary CT Angiographic Studies by Kuzo et al. pub. AJR:188, Mar. 2007 pp. 839-842 (Year: 2007).*

A New Device to Perform a Standardized Valsalva's Maneuver by Agarwal et al. pub. Chest. Feb. 1979;75(2):208-9. doi: 10.1378/chest.75.2.208b. PMID: 421563. (Year: 1979).*

International Search Report dated Jan. 5, 2015 for PCT/CH2014/000151, filed Oct. 14, 2014.

Written Opinion dated Apr. 23, 2015 for PCT/CH2014/000151, filed Oct. 14, 2014.

Ley Sebastian et al., XP055080600, "MRI Measurement of the Hemodynamics of the Pulmonary and Systemic Arterial Circulation: Influence of Breathing Maneuvrs", vol. 187, No. 2, dated Aug. 1, 2006.

J.T. Kowallick et al., XP009181735, Real-Time phase-contrast flow MRI of the ascending aorta and superior vena cava as a function of intrathoracic pressure (Valsalva manoeuvre), vol. 87, dated Sep. 16, 2014.

Result of Search Report for Switzerland No. 1787/13 dated Oct. 18, 2013.

Conrad Witram et al., "CT angiography of pulmonary embolism: diagnostic criteria and causes of misdiagnosis", Radiographics, Sep.-Oct. 2004, 21 pages.

Paul D. Stein et al., "Spiral computed tomography for the diagnosis ofacute pulmonary embolism", abstract, Throm. Haemost., 2007, 1 page.

S.W. Rathbun et al., "Sensitivity and specificity of helical computed tomography in the diagnosis of pulmonary embolism: a systematic review", abstract, Meta-Analysis: Ann Intern Med., Feb. 2000, 2 pages.

Marc V. Gosselin et al., "Contrast dynamics during CT pulmonary angiogram: analysis of an inspiration associated artifact", J. Thorac Imaging, Jan. 2004, vol. 19, No. 1, 8 pages.

Mortimer et al., "Use of expiratory CT pulmonary angiography to reduce inspiration and breath-hold associated artefact: contrast dynamics and implications for scan protocol", Clin Radiol., 2011, vol. 66, No. 12, pp. 1159-1166.

Chen et al., "Waiting to exhale: salvaging the nondiagnostic CT pulmonary angiogram by using expiratory imaging to improve contrast dynamics", Emerg Radiol., 2008, vol. 15, No. 3, pp. 161-169.

Wittram et al., "Transient interruption of contrast on CT pulmonaryangiography: proof of mechanism", abstract, J Thorac Imaging, 2007, 1 page.

"Use of expiratory CT pulmonary angiography to reduce inspiration and breath-hold associated artefact: Contract dynamics and implications for scan protocol", Correspondence, Clinical Radiology, 68, 2013, 1 page.

"Use of expiratory CT pulmonary angiography to reduce inspiration and breath-hold associated artefact: Contrast dynamics and implications for scan protocol. A reply", Correspondence, Clinical Radiology, 68, 2013, 2 pages.

Bernabé-Garcia et al., "Has 'respiratory coaching' before deep inspiration an impact on the incidence of transient contrast interruption during pulmonary CT angiography?", Insights Imaging, 2012, vol. 3, No. 5, pp. 505-511.

Kuzo, "Measurement of caval blood flow with MRI during respiratory maneuvers: implications for vascular contrast opacification on pulmonary CT angiographic studies", AJR Am J Roentgenol., Mar. 2007, vol. 188, No. 3, pp. 839-842.

Wexler et al., "Velocity of Blood Flow in Normal Human Venae Cavae", Circulation Research, 1968, 16 pages.

Kimura et al., "The effect of breathing manner on inferior venacaval diameter", abstract, Eur J Echocardiogr., Feb. 2011, 1 page.

Takata et al., "Superior and inferior vena caval flows duringrespiration: pathogenesis of Kussmaul's sign", abstract, Am J. Physiol., Mar. 1992, 1 page.

(56) References Cited

OTHER PUBLICATIONS

Gutzeit et al., "Suction against resistance: a new breathing technique to significantly improve the blood flow ratio of the superior and inferior vena cava", Eur. Radiol, 2014, vol. 24, pp. 3034-3041.
J.T. Kowallick et al., "Real-Time phase-contrast flow MRI of the ascending aorta and superior vena cava as a function of intrathoracic pressure (Valsalva manoeuvre)", Br J Radiol, vol. 87, 2014, 7 pages.
Sebastian Ley et al., "MRI Measurement of the Hemodynamics of the Pulmonary and Systemic Arterial Circulation: Influence of Breathing Maneuvers", Am J. of Roentgenology, 2006, vol. 187, p. 439-444.

* cited by examiner

BLOOD FLOW CONTROL SYSTEM AND METHODS FOR IN-VIVO IMAGING AND OTHER APPLICATIONS

FIELD OF THE INVENTION

The present invention relates to blood flow control systems, devices and methods, in particular to an imaging system for the human body, such as x-ray and related tomographic imaging systems.

BACKGROUND OF THE INVENTION

Images of the interior of the human body are a long-established tool for providing graphic information in form of pictures, prints and screen displays for a subsequent interpretation by skilled practitioners.

For many purposes detection of blood flow related conditions is an important part of such images. In order to improve the detection of blood flow conditions it is known that injection of a contrast medium into the blood stream can add information.

A well-known example of such methods is computer tomography (CT) angiography, which is widely accepted as standard method for the examination of patients with suspected pulmonary embolism and other vascular and parenchymal diseases. The advantages of CT are obvious: it is widely available, the method is rapid, and it is highly sensitive to nodules, embolus or clots in the blood stream.

To increase the image quality of the images generated by the CT scanner, it is further known that administration of a contrast agent during the scanning process enhances the vascular compartment and other fluids in the body, usually via venous access over the upper extremity such as via the back of the hand or via an elbow vein. Alternatively, it is also known to inject contrast material in the lower extremities. It is known that the contrast-enhanced blood flows through the superior vena cava (SVC) into the right atrium, while at the same time a volume of non-contrasted blood reaches the right atrium from the inferior vena cava (IVC). Evidently, the proportion of non-contrasted blood of the IVC in relation to the contrast enhanced SVC influences the dilution of contrast medium in the right atrium/ventricle, left atrium/ventricle and in the pulmonary artery (PA) and all subsequent arteries (e.g. coronary artery, carotid and brain arteries, and more distant arteries), in an effect known as transient interruption of the contrast bolus. This dilution influences potentially the diagnostic performance and quality of the entire investigation.

Several studies have been published on the effect of ventilatory activity on the blood flow as listed in the list of references below.

U.S. Pat. No. 6,631,716 suggests to set a defined volume of the lung despite respiration of a patient. No coordination of inhaling or exhaling with taking a MRI or CT is described and a contrast substance is not mentioned.

SUMMARY OF THE INVENTION

In the view of the above it is seen as an object of the invention to provide a specific dedicated device and its use, a scanning system and methods with improved and standardized flow accuracy and enhancement properties in the control of blood flow, dilution and enhancement properties for imaging of contrast enhanced blood flow (perfusion, first-pass enhancement, vascular supply of tumors, lesions and various tissues), particularly in relation to the vascular flow (perfusion, first-pass enhancement, arterial enhancement, improved detection of thromboembolic material within blood vessels, vascular space and supply of lesions, tumors and normal tissue) through the pulmonary artery or other arteries and veins as well as other vessels distally to the heart.

Hence, according to an aspect of the invention, there is provided a method of controlling and/or standardizing the distribution of a substance in the human body comprising the steps of applying a respiratory resistance device to the respiratory system of the body, and injecting the substance into the body and controlling or standardizing the distribution of the substance in the body through the selection of respiratory states characterized by a controlled interaction between the respiratory system of the body and the respiratory resistance device.

In another aspect, there is provided a method of acquiring in-vivo a series of images of interior parts of the human body, using an imaging system and including the steps of positioning a body relatively to the imaging system, applying a respiratory resistance device to the respiratory system of the body, and performing the image acquisition step during an inhalation, inspiration or suction phase, during which the body exercises suction against a resistance as provided by the respiratory resistance device. Alternatively or in addition, the image acquisition step is performed during the exhalation phase.

The imaging system can be a scanner using an x-ray imaging method, a scanner using magnetic resonance imaging or ultrasound imaging method including for example scanners for angiography, CT scanners, MR and positron emission based variants such as PET/CT or SPECT/CT, PET/MRI or ultrasound scanners.

The respiratory resistance device includes preferably an inner volume with an opening or openings in direction towards the physiological openings (nose, mouth) of the respiratory system of the body and essentially no or only small openings or leaks towards the environment. The dimensions of the volume and the openings are selected such that a normal untrained patient can achieve an underpressure (in the case of suction or inspiration against resistance) or an overpressure (in the case of exhalation against resistance or Valsalva) in the inner volume of the device and, preferably, maintain such pressure for the duration of the image acquisition, e.g. preferably between 1 and 60 seconds and preferably between 5 and 45 seconds and preferably between 5 and 30 seconds. The preferred pressure range for such an underpressure is −1 up to −80 mmHg and preferably up to −60 mmHg and preferably up to −40 mmHg, more preferably −8 to −20 mmHg. For overpressure a preferred range is +1 to +80 mmHg, more preferably +10 to +30 mmHg with the pressure 0 mmHg being gauged to equal atmospheric pressure.

In a preferred embodiment, the respiratory resistance device includes a replaceable and disposable mouth piece to connect the inner volume of the device with the respiratory system of the body. The mouth piece can be for example a tube or a modified tube, e.g., with an elliptical or round cross-section or with a specifically designed end for ease of use when applied to the mouth. However, in cases where it is preferred to include all openings of the respiratory system of the body, the mouth pieces can also be shaped as a mask.

It is preferred that a mouth piece fits closely and thus tightly with the resistance device. A mouth piece may also fit with defined spaces for the exit or entry of air between mouth piece and resistance device. A mouth piece may as well be formed integral with the resistance device.

In a further preferred embodiment, the respiratory resistance device includes or is coupled to a sensor for measuring a parameter indicative of the pressure inside the inner volume of the device. The measurement can be displayed in a numerical form or as acoustic or optical signals or symbols, preferably indicating in operation whether the inhaling/inspiration/suction or exhaling/expiration/valsalva, respectively, is to be increased or decreased in intensity to achieve an optimal and/or steady-state pressure.

The respiratory resistance device is best operated in parallel to and in conjunction with the image acquisition of the image acquisition system and preferably also in parallel and in conjunction with an injection system for injecting of a contrast medium or other diagnostic substance into a venous vessel of the body. The device can however also be used without injection of supplementary contrast agent. If performed with contrast agent administration it is preferred to use injection into the upper extremity or lower extremity in the case of an inhaling or suction action and injection into vessels of the lower extremity in the case of an exhaling or Valsalva action. The timings of these two or three parallel operations are chosen such that all operations are concurrently effective (well coordinated outside and in the body) during the actual image acquisition or any other administration step.

In a variant the respiratory resistance device and the image acquisition device are linked. The link can be implemented in form of a data communication link or in form of a partial or full incorporation of the elements of the respiratory resistance device into the image acquisition system and/or injection system.

Further aspects of the invention include the respiratory resistance device, a combination of respiratory resistance device and the image acquisition system, preferably in combination with an injection system, and any images acquired by the use of the above methods and/or devices or combination of devices and scanning systems.

The invention is particularly useful in improving the enhancement and image acquisition related to various steps of angiography of the pulmonary arteries or other arteries and veins in the rest of the body (perfusion, first-pass vascular enhancement, vascular supply of tumors, lesions and various tissues, detection of thromboembolic material).

The invention can be further used in methods and devices for administration, preferably intraveneous, of a substance in order to control or standardize the distribution and/or concentration of such a substance in the body.

The respiratory resistance device of the invention can be used in general to influence via defined respiratory states the distribution and/or standardization of blood supply either from the upper, superior vena cava or lower, inferior vena cava according to the respective requirement of any medical or technical conditions such as the task to increase blood supply from the respective vessel to the right atrium of the heart or enhance the concentration of an injected substance in the blood flow in the pulmonary arteries or in vessels beyond the pulmonary arteries. This can be extended to applications such as drug injection through the upper or lower peripheral veins, invasive procedures, surgery or any blood supply related indication The methods, the devices and systems and their use are in particular able to control and standardize blood flow to perform high contrast density within arteries and/or veins, such as pulmonary vessels, brain vessels, vessels of visceral organs or vessels of the extremities or other vessels within a human or animal body. Standardized blood flow increases contrast density in the above vessels, increasing image quality of images taken with imaging systems such as mentioned. On the other hand the methods, devices and systems and their use may allow to reduce the amount of contrast substances.

The above and other aspects of the present invention together with further advantageous embodiments and applications of the invention are described in further details in the following description and figures.

DETAILED DESCRIPTION

Figure 1A:
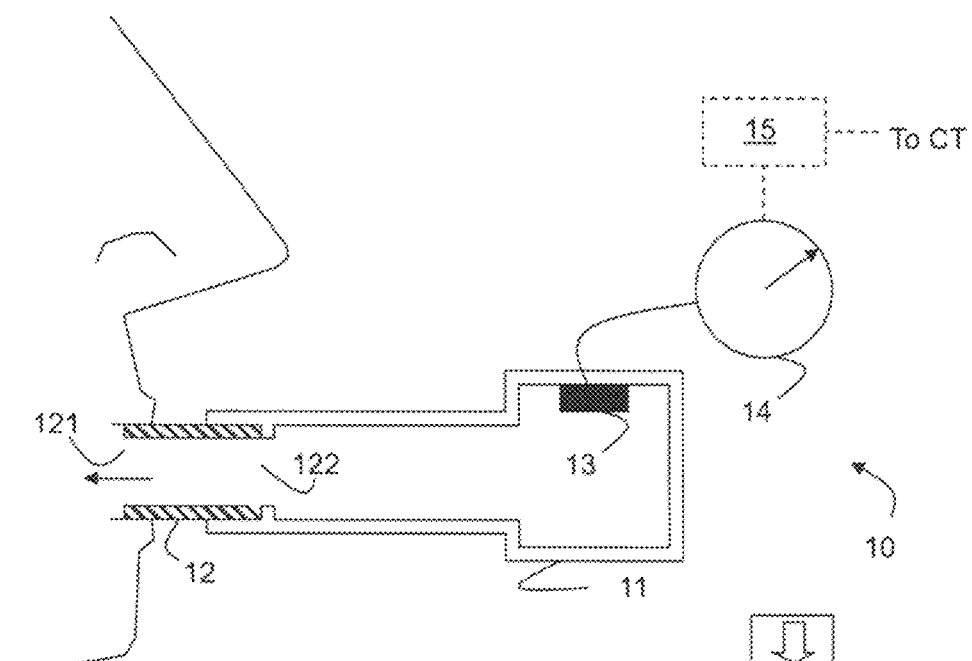
FIG. 1A is a schematic cross-section of a respiratory restriction device in accordance with an example of the invention.

An exemplary respiratory resistance device 10 is shown in FIG. 1A. The device has a main body 11 of resilient material such as Teflon® or stainless steel or other similar materials. The main body provides a cap and holder for a disposable mouthpiece 12. The mouth piece and the main body are connected to each other by a simple form fitting attachment so that the mouth piece can be easily attached and removed from the main body by a straight insertion and extraction movement, preferably without involving a twist or use of a tool. Any similar form or attachment method might be suitable.

The mouth piece 12 has an essentially tubular, hollow shape with a proximate opening 121 adapted for insertion into a patient's mouth and a distal opening 122 providing a flow connection into the interior of the main body 11.

It should be however clear that materials, dimensions and shapes of the main body 11 and the mouthpiece can vary widely while still maintaining the function of providing resistance against free breathing. For example, it is possible to shape the proximate opening more ergonomically or give the cross-section a more elliptical circumference. Such and similar modifications can, however, be regarded as being well within the scope of an ordinarily skilled person.

Further mounted onto the main body 11 is a pressure sensitive device 13, which can be for example a piezoresistive transducer integrated with processing circuits onto a silicon substrate. Such sensors are commercially available for example as MPXV7002 from Freescale Semiconductor Inc.

The sensor 13 is connected to a control signal generator 14. The control signal can be a numeric display of the pressure in the interior of the main body as shown. However the control signal can alternatively or in addition be an acoustic signal or an optical signal selected according to predefined pressure thresholds or ranges. The respiratory resistance device 10 of FIG. 1 can as well omit the pressure sensitive device 13 and will work in this very simple form as well.

Thus the control signal generator 14 can give a patient or an operator of a scanning or injection apparatus a feedback on the ventilatory activity or respiratory state of the patient during the image acquisition by the scanner or during a controlled injection of a substance. The respiratory device, the methods connected therewith and its use are able to control and standardize blood flow within patients related veins arteries during CT or MRI or other diagnostic procedures. In particular it can be indicated whether or not a patient is in the desired ventilatory activity or respiratory state or whether the patients breathing should be adapted or even changed to reach the desired state, e.g. in case of inhalation/suction whether the patient should inhale suck stronger, less strong or steady. It is for example possible to use a programmable microcontroller (not shown) as part of the control signal generator 14 so as to control a display or color coded lights depending on the parameter as measured by the sensor 13 as feedback to patient and/or operator.

Optionally the sensor 13 can be connected to a synchronizing element 15 that is also linked to the image acquisition system. The link can be for example a wired, a wireless or an optical link for data transmission. Such an element can be used to combine information from the ventilatory or breathing activity of the patient (device) with the images acquired by any image acquisition system. This would enable a manual or automated selection of images acquired during the desired state of ventilatory activity even where this activity is fluctuating (around the desired state) during the scan. For example the synchronizing element can include a display of pressure values along with the date and temporal information of the image acquisition. Corresponding time stamps may be included on the acquired image.

Figure 1B:
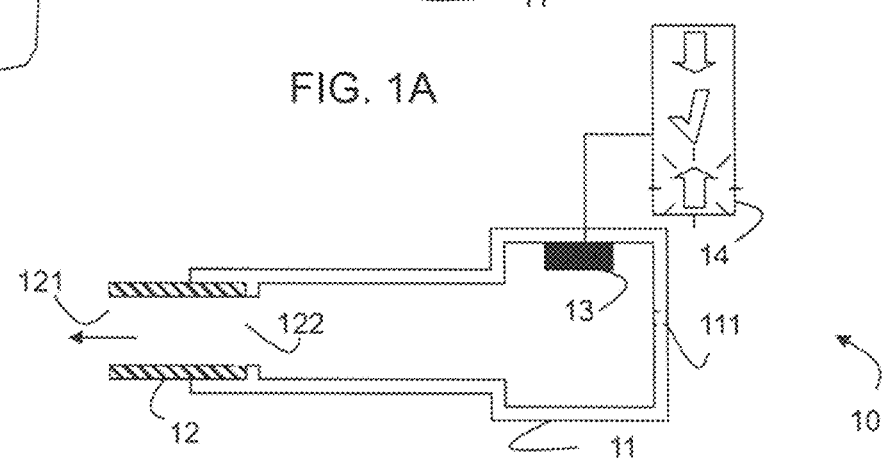
FIG. 1B is a schematic cross-section of a variant of the respiratory restriction device of FIG. 1A.

In the example of FIG. 1B the main body 11 includes a small opening 111 to the exterior to allow for a limited air flow into or from the interior and hence into or out of the patient's respiratory system. The dimensions of the opening 111 are in such a case selected so as to provide sufficient air flow resistance or restriction to prevent normal (abdominal) breathing. Small openings allowing a controlled air flow can be advantageous in order to achieve a controlled and steady state inflow of air or other respiratory gases (oxygen, xenon or other). Such an opening 111 or multiple openings may alternatively or additionally be present on the mouth piece or may be formed by the connection means of mouth piece and main body.

The control signal generator 14 of the example of FIG. 1B is designed as an optical indicator showing a patient in simplified symbols whether to increase or decrease the breathing efforts.

Figure 1C:
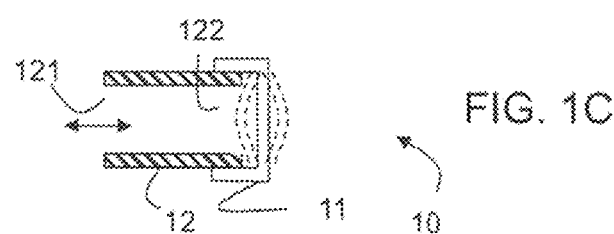
FIG. 1C shows a schematic cross-section of another simplified respiratory restriction device in accordance with an example of the invention.

However, it is worth noting that the respiratory resistance device does not necessarily require any electronic components or any sensors to perform the function of an air flow resistance or restriction. If, for example, a simpler, more cost efficient device is required, the main body 11 can be embodied or replaced, respectively, by a simple cap over the opening 122 of the mouth piece as shown in FIG. 10. If parts of the cap are designed as flexible or moveable, then the ventilatory activity can be monitored by the movement or deformation of such parts. A thin membrane in the cap or elsewhere along the tube would for example bulge in or out depending on the pressure generated by the patient during in- or exhaling as indicated in FIG. 1C by the dashed lines. Other examples can include a movable object or column of liquid placed in a tube and moving in dependence of the ventilatory activity of the patient. Such variants would still be sufficient to implement examples of the present invention.

The tube or mouth piece can be adapted for use with nasal openings or with both mouth and nose. In the latter cases, it is advantageous to use a mask type connector as mouth piece between the main body 11 of the respiratory resistance device 10 and the respiratory system of the patient instead of a tubular connector. The mask would be typically designed (e.g. with an elastic lip at its circumference) to provide sufficient air tightness to still function as a resistance against free breathing. It is further worth noting that the respiratory resistance device is not intended to provide breathing assistance during the scan as may be applied to support breathing for patients with significant respiratory failures. Thus, the known breathing masks connected to breathing support elements such as bellows or gas supply are not understood as respiratory resistance device within the meaning of the present invention.

It is further contemplated to integrate the respiratory resistance device 10 into an image acquisition system used to acquire images of the interior of the patient's body. In such a variant at least part of the main body 11, in particular the sensor 13, the control signal generator 14 and/or the synchronizing element 15 and related circuitry would be located within the housing of the image acquisition system and for example connected to the mouth piece by means of an elongated, essentially air-tight flexible tube. Such an integration has the advantage of reducing the number of separate parts in an area which best contains only essential equipment.

In some applications, the respiratory resistance device 10 is operated typically simultaneously with the operation of the image acquisition system. The image acquisition system can be a computer tomography (CT) scanner or a magnetic resonance imagine device (MRI), Angiography, PET/CT, PET/MRI, any ultrasound imager and other similar imaging devices.

In such applications the patient is positioned within the image acquisition system with the respiratory resistance device applied to either mouth and/or nose. To enhance the contrast of any images acquired, a contrast medium, for example iodine based contrast fluid, ultrasound contrast agent or Gadolinium based contrast material, is injected through a venous vessel of the patient. The respiratory resistance device, the methods and systems may be operated together with the injection system for injecting the contrast enhancing substance.

Details of a method of acquiring in-vivo images of the interior of a human or animal body in accordance with an example of the present invention are described in the following making reference to FIG. 2.

Figure 2:
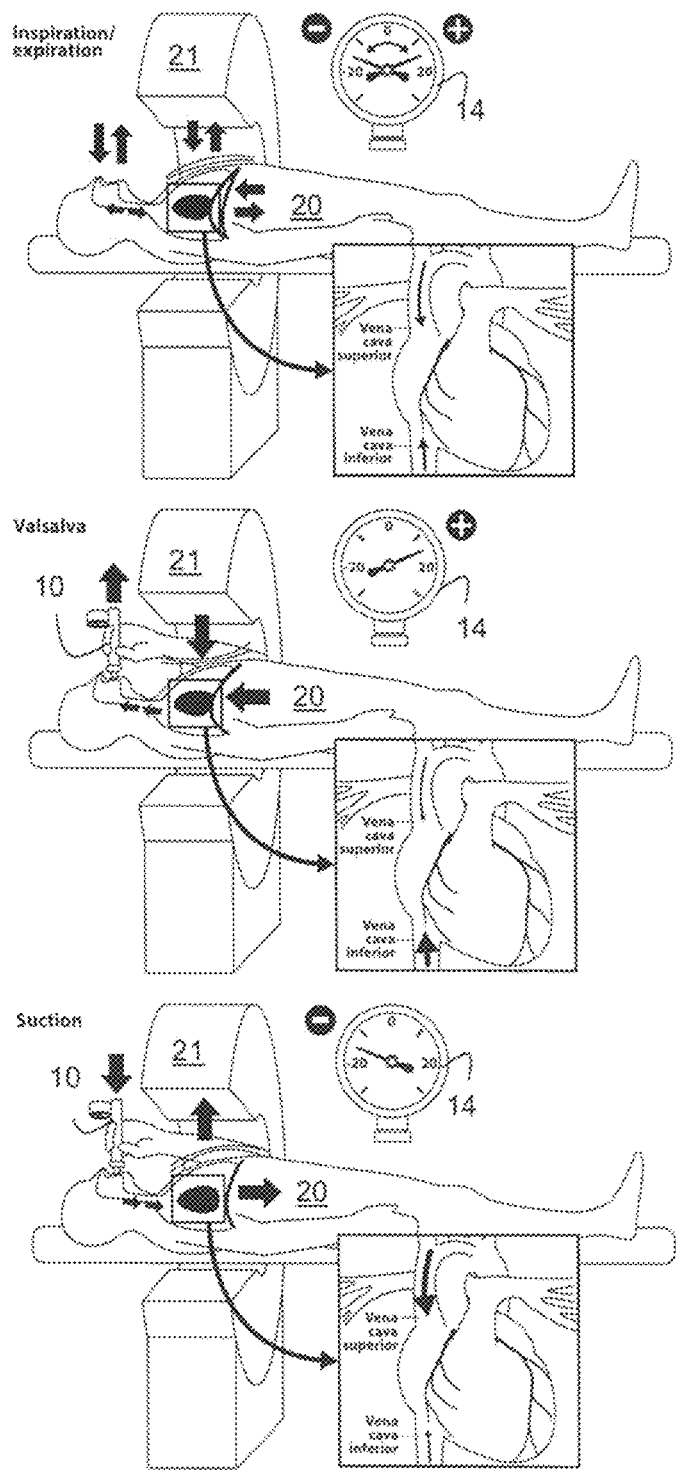
FIG. 2 illustrates schematically different respiratory states during an image acquisition.

In FIG. 2 there is shown a patient 20 being positioned horizontally within the tunnel of a scanner 21, which can be for example a CT scanner or an MRI scanner. A respiratory resistance device 10 in accordance with an example of the invention is placed on the mouth of the patient 20. An injection system for administering a contrast fluid is connected to a venous vessel of the patient but not shown as such systems are well known in the state of the art.

The three panels of FIG. 2 illustrate three different respiratory states of the patient as can be registered by the respiratory resistance device 10. The enlarged detail shows a simplified representation of the human heart together with the blood flow through the vena cava superior SCV (entering the right atrium from above) and through the vena cave inferior ICV (entering the right atrium from below).

The respiratory states are characterized in the figure by arrows indicating predominant direction of air or blood flow or diaphragm movements including movements of the lung, respectively, on the one hand and by the meter 14 readings as displayed on the other.

The upper panel represents the basic conditions under which for example PA images are presently acquired. It is characterized herein as free breathing with no respiratory resistance device 10 in place. The air is moved into and out of the respiratory system of the human body 20 as indicated by the arrows in the area of the head. At the same time the thorax moves up and down as indicated by the arrow in the chest region of the patient 20. The breathing is typically accompanied by movement of the diaphragm as indicated by the arrows in the abdominal region of the patient 20. A flow or pressure measurement 14 shows a swing to and fro between positive or negative values (representing inflow (suction) or outflow (Valsalva) of air or a swing between under- or overpressure as would be measured when using the respiratory resistance device during this state of free breathing).

The respective blood flows through the ICV and SCV are as normal indicated by the two arrows of equal line thickness in the enlarged view. No change or contrast enhancement is expected in this respiratory state.

In the middle panel a respiratory state characterized as Valsalva maneuver is illustrated. In this state the patient breathes into the closed or flow restricted inner volume of the respiratory resistance device 10. The arrows in the head region indicate the direction in which the air flow is directed. The thorax moves inwards and the diaphragm upwards towards the thorax. The sensor registers this Valsalva state as overpressure typically in the range of 1 to 100 mbar for an untrained patient attempting to maintain a constant pressure for the period of the scan between 1 and 60 seconds, preferably between 5 and 45 seconds.

Again a contrast agent or any type of dye can be injected into the patient's body 20 shortly before and/or during the Valsalva state. A change from normal in the respective flows through the ICV and SCV can be observed as indicated by the arrow in the ICV being thicker than the respective arrow in the SCV. This indicates that the Valsalva state can favor the venous blood flow from the extremities of the lower body. This provides an indication that by administering a contrast medium into a venous access in a lower extremity during the image acquisition step an improved and/or more stable contrast enhancement can be achieved.

To achieve this enhancement it can be necessary to maintain the Valsalva status during the scan acquisition and even injection or, conversely, to interrupt the scanning process during periods in which the patient exits the Valsalva state or discard or mark images obtained outside the optimal Valsalva state. For such operations the monitoring as provided by the respiratory resistance device is advantageous.

In the lower panel of FIG. 2 a respiratory state is illustrated characterized as breathing against resistance or anti-Valsalva maneuver. In this state the patient 20 sucks air from the closed or flow restricted inner volume of the respiratory resistance device 10. Again the arrows in the head region indicate the direction in which the air flow is directed. The thorax moves outwards and the diaphragm downwards towards the lower body. The sensor 14 registers this state as underpressure typically in the range of −1 to −60 mmHg for an untrained patient attempting to maintain a constant pressure for the period of the scan between 1 and 60 seconds, preferably between 5 and 45 seconds.

Again a contrast fluid or another substance can be injected into the patient's body 20 shortly before and/or during the anti-Valsalva (suction against resistance) state. A change from normal in the respective flows through the ICV and SCV can be observed as indicated by the arrow in the SCV being thicker than the respective arrow in the ICV. This indicates that the anti-Valsalva state favors the venous blood flow from the extremities of the upper body. This provides an indication that by administering the contrast medium into a venous access in an upper extremity or a lower extremity during the image acquisition step an improved and/or more stable contrast enhancement can be achieved. To achieve this enhancement it can be necessary to maintain the anti-Valsalva state for the duration of the scan or, conversely, to interrupt the scanning process during periods in which the patient exits the anti-Valsalva state or discard or mark images obtained outside the anti-Valsalva state. Again, the presence or absence of such states is enabled and monitored by the respiratory resistance device 10.

Figure 3:
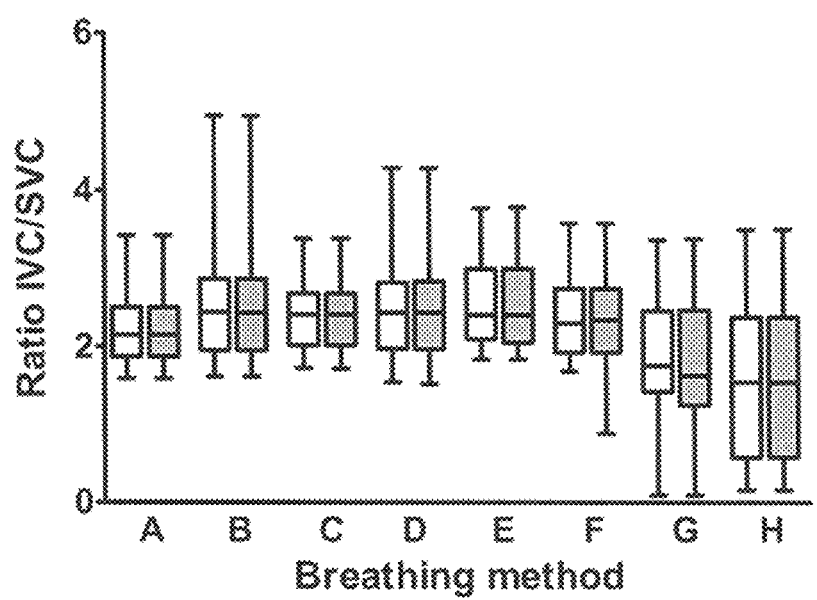
FIG. 3 is a graph of test results indicating mixing ratios between flow from the vena cave superior vs flow from the vena cava inferior depending on respiratory states.

Test results using various standardized breathing states or maneuvers and flow-sensitive MR phase contrast techniques in the SVC and IVC and imaged in the supine position on a 1.5 Tesla MRI unit (Achieva 1.5 T, Phillips Healthcare, Best, The Netherlands) are shown in FIG. 3 using an 8-channel torso coil (Philips Health care) covering the entire chest allowing the regular acquisition of two sets of heart triggered dynamic phase contrast (PC) images (TR 50 msec and TE 4 msec; Slice thickness 8 mm, flip angle 15°, velocity encoding 100 msec; voxel size 1.9×2.5) in the axial section of the SVC and IVC.

In order to guarantee standardized and reproducible breathing an MR-compatible respiratory resistance device was used for controlling and monitoring the respiratory pressure and blood flow during the entire maneuvre. Besides the newly defined breathing method "suction against resistance", previously defined techniques such as valsalva, apnea after end of inspiration, apnea after end of expiration and free breathing are also investigated allowing comparison with known studies (see references).

The capital letters in FIG. 3 indicate the respiratory state or the interaction with the respiratory resistance device, where used. IVC/SVC ratios for stroke volumes (white boxes) and flux (grey boxes) are shown for free breathing (A), end of inspiration position with breath hold (B), end of expiration position with breath hold (C), Valsalva maneuver at +10 mm Hg (D), Valsalva maneuver at +20 mm Hg (E), Valsalva maneuver at +30 mm Hg (F), suction maneuver at −10 mm Hg (G), similar suction maneuver at −20 mm Hg (H). Boxes show the median and the 25th and 75th quartiles; whiskers show minimum and maximum values. The optimal ratio is achieved in the suction mode with thoracic underpressure, but standard deviations are higher, demonstrating more unstable conditions. Other states such as the Valsalva maneuver can be considered, too, but show a much reduced effect under these circumstances.

It should be noted that the method and respiratory device as described in the example using an MRI scanner above may work equally well or even better in connection with a CT scanner or other imaging or diagnostic techniques.

Figure 4:
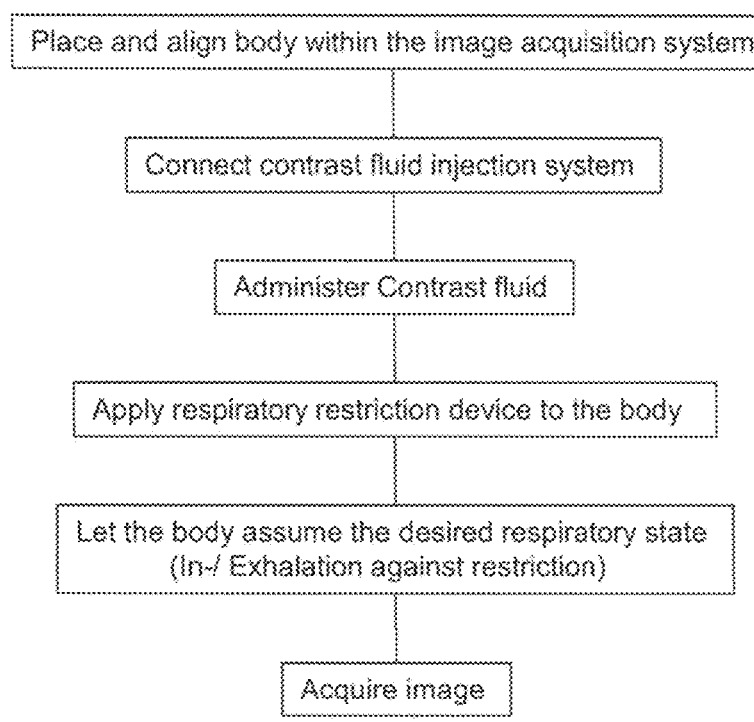
FIG. 4 illustrates steps in accordance with an example of the invention.

The steps performed on a patient are summarized in the flow chart of FIG. 4. However it should be noted that the sequence of steps as shown in FIG. 4 is not indicative of a specific temporal order of such steps as most of the steps are best undertaken simultaneously to achieve the better results.

It should be noted that the above methods and devices can be used in any method requiring control or standardization of the mixing of the flow of blood from the IVC und SVC, and can be effective even in the blood circulation beyond the pulmonary arteries and the lungs, e.g., into the peripheral organs and body parts. Such a control and standardization can enable for example the improved performance of first pass measurements or perfusion, particularly for tumors or other vessels and tissues, or the distribution of drugs or dyes into the body, particularly where such drugs or dyes are administered intravenously.

When used with a contrast medium suited for ultrasound acquisition system, such as gas bubbles, the above methods and devices can also be applied to image acquisitions using an ultrasound scanner.

While there are shown and described presently preferred embodiments of the invention, it is to be understood that the invention is not limited thereto but may be otherwise variously embodied and practised within the scope of the following claims.

LIST OF REFERENCES

1. Wittram C, Maher M M, Yoo A J, Kalra M K, Shepard J A, McLoud T C. CT angiography of pulmonary embolism: diagnostic criteria and causes of misdiagnosis. Radiographics. 2004; 24: 1219-1238.
2. Stein P D, Kayali F, Hull R D. Spiral computed tomography for the diagnosis of acute pulmonary embolism. Thromb Haemost. 2007; 98: 713-720.
3. Rathbun S W, Raskob G E, Whitsett T L. Sensitivity and specificity of helical computed tomography in the diagnosis of pulmonary embolism: a systematic review. Ann Intern Med 2000; 132:227-232.
4. Gosselin M V, Rassner U A, Thieszen S L, Phillips J, Oki A. Contrast dynamics during CT pulmonary angiogram: analysis of an inspiration associated artifact J Thorac Imaging. 2004; 19: 1-7.
5. Mortimer A M, Singh R K, Hughes J, Greenwood R, Hamilton M C. Use of expiratory CT pulmonary angiography to reduce inspiration and breath-hold associated artefact: contrast dynamics and implications for scan protocol. Clin Radiol. 2011; 66: 1159-1166.
6. Chen Y H, Velayudhan V, Weltman D I, Balsam D, Patel N, Draves K A, Robinson K A, Vu T H. Waiting to exhale: salvaging the nondiagnostic CT pulmonary angiogram by using expiratory imaging to improve contrast dynamics. Emerg Radiol. 2008; 15: 161-169.
7. Wittram C, Yoo A J. Transient interruption of contrast on CT pulmonary angiography: proof of mechanism. J Thorac Imaging. 2007; 22: 125-129.
8. Arenas-Jiménez J, Bernabé-García J, García-Espasa C. Re: Use of expiratory CT pulmonary angiography to reduce inspiration and breath-hold associated artefact: contrast dynamics and implications for scan protocol. Clin Radiol. 2013; 68(2).
9. Hamilton M C, Mortimer A M, Hughes J. Re: Use of expiratory CT pulmonary angiography to reduce inspiration and breath-hold associated artefact: contrast dynamics and implications for scan protocol. A reply. Clin Radiol. 2013; 68(2):e99-100.
10. Bernabé-García J M, García-Espasa C, Arenas-Jiménez J, Sánchez-Payá J, de la Hoz-Rosa J, Carreres-Polo J O. Has "respiratory coaching" before deep inspiration an impact on the incidence of transient contrast interruption during pulmonary CT angiography? Insights Imaging. 2012; 3: 505-511.
11. Kuzo R S, Pooley R A, Crook J E, Heckman M G, Gerber T C. Willeput Measurement of caval blood flow with MRI during respiratory maneuvers: implications for vascular contrast opacification on pulmonary CT angiographic studies. AJR Am J Roentgenol. 2007; 188:839-842
12. Wexler L, Bergel D H, Gabe I T, Makin G S, Mills C J. Velocity of blood flow in normal human venae cavae. Circ Res. 1968; 23: 349-359
13. Kimura B J, Dalugdugan R, Gilcrease G W 3rd, Phan J N, Showalter B K, Wolfson T. The effect of breathing manner on inferior vena caval diameter. Eur J Echocardiogr. 2011; 12:120-123
14. Takata M, Beloucif S, Shimada M, Robotham J L. Superior and inferior vena caval flows during respiration: pathogenesis of Kussmaul's sign. Am J Physiol. 1992 March; 262(3 Pt 2):H763-70

The invention claimed is:

1. A method of acquiring in-vivo an image of interior parts of a body of a patient having a respiratory system and a blood circulation system, the method comprising:
    positioning the body relative to an imaging system;
    applying a respiratory resistance device to the respiratory system of the body, the respiratory resistance device having a mouthpiece connected to a main body portion, the main body portion either closed to an exterior environment or having one or more openings to the exterior environment dimensioned to restrict air flow in an inner volume of the respiratory resistance device during inhalation;
    performing an image acquisition step with the imaging system during a defined respiratory stat of suction against resistance, which is an inhalation phase during which the body provides suction against a resistance provided by the respiratory resistance device such that an under pressure is generated in the inner volume of the respiratory resistance device during inhalation; and
    administering a contrast fluid or a dye into a venous access in an upper or a lower extremity of the body before or during the inhalation phase such that, after administering the contrast fluid or dye, the contrast fluid or dye flows in the blood circulation system of the body,
    wherein the under pressure that is generated in the inner volume of the respiratory resistance device during inhalation in the defined respiratory state of suction against resistance is in a range of −8 to −20 mmHg.

2. The method of claim 1, wherein the image acquisition is performed while applying the respiratory resistance device to the respiratory system during the inhalation phase such that the inhalation reduces pressure in the inner volume of the respiratory resistance device relative to a pressure in the inner volume of the respiratory device in the absence of inhalation.

3. The method of claim 2, wherein the inhalation is maintained for at least 1 second.

4. The method of claim 1, wherein the imaging system is a computer tomographic (CT) scanner, a ultrasound scanner or a magnetic resonance image (MRI) scanner.

5. The method of claim 1, further comprising monitoring a parameter related to a pressure generated by the inhalation during the image acquisition, and using the monitored parameter to generate an indication of a deviation from an optimal inhalation state.

6. The method of claim 1, wherein the main body portion of the respiratory resistance device comprises the one or more openings to the exterior environment dimensioned to restrict air flow in the inner volume of the respiratory resistance device during inhalation so as to generate the under pressure in the inner volume of the respiratory resistance device during the inhalation phase.

7. The method of claim 1, wherein the mouthpiece is replaceable.

8. The method of claim 1, wherein the respiratory resistance device includes a sensor for measuring a parameter related to pressure in the inner volume.

9. The method of claim 8, wherein the respiratory resistance device further comprises an indicator for indicating deviation of the parameter measured by the sensor from a preset pressure value or range of pressure values.

10. The method of claim 9, wherein the indicator indicates whether the parameter measured by the sensor is lower than a preset lower limit or higher than a preset upper limit.

11. The method of claim 1, wherein performing the image acquisition step comprises imaging of blood flow that is enhanced by the contrast fluid or dye relative to imaging of blood flow in the absence of the contrast fluid or dye.

12. The method of claim 1, wherein the image acquisition is angiographic image acquisition.

13. The method of claim 1, wherein the defined respiratory state changes respiratory pressure during the image acquisition step.

14. The method of claim 1, wherein the main body portion of the respiratory resistance device is closed to the exterior environment so as to completely block flow of air from the respiratory system to the atmosphere.

15. A method of acquiring in-vivo an image of interior parts of a body of a patient having a respiratory system and a blood circulation system, the method comprising:
    positioning the body relative to an imaging system;
    injecting a contrast medium into a venous vessel of the body such that, after injecting the contrast medium, the contrast medium flows in the blood circulation of the body;
    applying a respiratory resistance device to the respiratory system of the body;
    having the patient breathe through the respiratory resistance device, the respiratory resistance device providing resistance to breathing; and
    using the imaging system to acquire an image during a defined respiratory state of suction against resistance, which is an inhalation phase of breathing during which the body provides suction against the resistance provided by the respiratory resistance device such that an under pressure is generated in an inner volume of the respiratory resistance device during inhalation, the image being of interior parts of the body,
    wherein the under pressure that is generated in the inner volume of the respiratory resistance device during inhalation in the defined respiratory state of suction against resistance is in the rage of −8 to −20 mmHg.

16. The method of claim 15, wherein the respiratory resistance device has a mouthpiece connected to a main body portion, the main body portion being closed to an exterior environment as to completely block flow of air from the respiratory system to the atmosphere.

17. The method of claim 15, wherein the respiratory resistance device has a mouthpiece connected to a main body portion, the main body portion comprising one or more openings to the exterior environment dimensioned to restrict air flow in the inner volume of the respiratory resistance device during inhalation.

\* \* \* \* \*